United States Patent
Liu et al.

(10) Patent No.: US 9,809,617 B2
(45) Date of Patent: Nov. 7, 2017

(54) CRYSTAL FORM OF REGADENOSON AND PREPARATION METHOD THEREOF

(71) Applicant: Shanghai Ziyuan Pharmaceutical Co., Ltd., Minhang, Shanghai (CN)

(72) Inventors: Wei Liu, Shanghai (CN); Zhigang Zhang, Shanghai (CN); Qin Bao, Shanghai (CN)

(73) Assignee: Shanghai Ziyuan Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 14/791,290

(22) Filed: Jul. 3, 2015

(65) Prior Publication Data
US 2017/0002036 A1 Jan. 5, 2017

(51) Int. Cl.
*C07H 19/16* (2006.01)
*C07H 19/167* (2006.01)

(52) U.S. Cl.
CPC ........... *C07H 19/16* (2013.01); *C07H 19/167* (2013.01)

(58) Field of Classification Search
None
See application file for complete search history.

(56) References Cited

U.S. PATENT DOCUMENTS 6,403,567 B1 6/2002 Zablocki et al.
7,732,595 B2 6/2010 Zablocki et al.

FOREIGN PATENT DOCUMENTS

| IT | WO 2014167046 A1 * | 10/2014 | ........... C07H 19/167 |
| WO | WO-2012/149196 A1 | 11/2012 | |

* cited by examiner

*Primary Examiner* — Layla Berry
(74) *Attorney, Agent, or Firm* — Honigman Miller Schwartz and Cohn LLP; Matthew H. Szalach; Jonathan P. O'Brien

(57) ABSTRACT

The present invention relates to the field of medicinal chemistry, and discloses a new crystal form of regadenoson, i.e., a crystal form E of regadenoson, as well as a method for preparing the new crystal form of regadenoson. The crystal form E of regadenoson according to the present invention has excellent performances in terms of radionuclide myocardial perfusion imaging, and has a poor toxicity, good storage stability, and can be used in the preparation of a medicament used as a stress agent for radionuclide myocardial perfusion imaging.

6 Claims, 4 Drawing Sheets

CRYSTAL FORM OF REGADENOSON AND PREPARATION METHOD THEREOF

FIELD OF THE INVENTION

The present invention relates to the field of pharmaceutical chemistry, specifically to a new crystal form of regadenoson and a method for preparing the same.

BACKGROUND OF THE INVENTION

This section provides background information related to the present disclosure which is not necessarily prior art.

Regadenoson, which chemical name is (1-{9-[(4S,2R,3R,5R)-3,4-dihydroxy-5-(hydroxymethyl)oxolan-2-yl]-6-aminopurin-2-yl}pyrazol-4-yl)-N-methylcarboxamide, has a structural formula as follows:

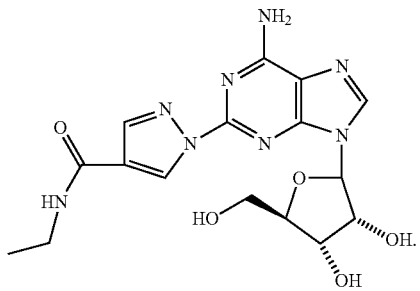 [SMILES: CCNC(=O)c1cnn(-c2nc(N)c3ncn(C4O[C@H](CO)[C@@H](O)[C@H]4O)c3n2)c1]

U.S. Pat. No. 6,403,567B1 firstly disclosed regadenoson as well as a preparation method and use thereof. Regadenoson is an adenosine A2A receptor agonist with high selectivity, used as a stress agent for radionuclide myocardial perfusion imaging, which has been clinically applied as a cardiac vasodilator for cardiac imaging in USA.

Polymorphism in pharmaceuticals is a common phenomenon in drug research and development, and is an important factor which influences drug quality. Polymorphism refers to a phenomenon that the same compound can form two or more molecularly spatial arrangements by controlling different generation conditions, thus to generate different crystalline solids. Different crystal forms of the same compound have the same chemical composition, but have different crystal microstructures, thus leads to difference in their morphological appearance, physicochemical property and bioactivity. Different crystal forms of a drug often have different solubility, storage stability, hygroscopicity, density and bioavailability. The crystal form of a drug directly affects the quality and absorption behavior in human body of a pharmaceutical preparation of the drug, and finally affects the benefit ratio between the therapeutic effect and side effect of the preparation in human body. Therefore, researches on the polymorphism of a drug and preparation methods for different crystal forms thereof are of great significance.

Currently, it is known that regadenoson exists in various crystal forms. U.S. Pat. No. 7,732,595 disclosed many crystal forms of regadenoson, including crystal forms A, B, C, and an amorphous form.

Crystal form A (as shown in FIG. 1) was produced by crystallization from a protic solvent or a polar solvent, such as ethanol or a mixed solvent of ethanol and water, or a mixed solution of N,N-dimethylsulfoxide and water. Crystal form A is a monohydrate, and is the most stable among the various crystal forms of regadenoson, which is stable under heating under relative humidity stress conditions up to its melting point. However, due to the very poor solubility of regadenoson, it is mostly insoluble in common solvents, is slightly soluble in water, and is difficult to be dissolved by a mixed solvent of protic solvents alcohols and water. As such, crystal form A is not suitable for scale production and preparation. Moreover, when crystal form A is prepared by using a mixed solution of DMSO and water, it is very difficult to remove DMSO thoroughly due to its extremely high melting point up to 189° C., thus failing to obtain crystal form A at a high purity.

Crystal form B (as shown in FIG. 2) was a crystal form obtained by dissolving regadenoson in a solvent trifluoroethanol at ambient temperatures followed by concentrating under reduced pressure. Such a crystal form was distinctly different from other crystal forms, which X-ray analysis gave disordered broad peaks. The crystal form contains varying amounts of crystal water, and it is very difficult to reproduce the preparation process thereof.

A new crystal form solid obtained by slurrying regadenoson in acetonitrile for a long time at 60° C. followed by filtration, is crystal form C (as shown in FIG. 3). Such a crystal form also contains uncertain content of crystal water, and is unstable after losing crystal water under a high temperature.

The amorphous form of regadenoson was formed by heating crystal form A up to 200° C., which, however, is unstable in atmospheric moisture, forming various crystalline hydrates thereof.

International Patent WO2012149196 reports crystal form D of regadenoson (as shown in FIG. 4) and a preparation method thereof. Regadenoson was dissolved in a mixed solution of methanol and water via reversed phase chromatography, and concentrated to a paste; the paste was heated in an oil-bath to 150° C. under a reduced pressure of 20 mmHg for 6 hours to afford crystal form D as a white solid, which contained 0.8-1.7% of crystal water. However, the method as described in this patent is a too complicated and rigorous process, is difficult to be reproduced and scaled up, and needs to be heated to a high temperature up to 150° C. which easily causes the decomposition of the compound.

SUMMARY OF THE INVENTION

In view of this, the present invention aims to study, discover and provide a new crystal form of regadenoson and a method for preparing the same through a crystallography method.

The present invention studies, discovers and provided a new crystal form of regadenoson, i.e., crystal form E of regadenoson.

In the present invention, X-ray powder diffraction (XRPD), which is internationally acknowledged, is adopted to study and characterize the new crystal form of regadenoson. Instrument equipment: D/MAX-1200 X-ray powder diffractometer. Assay conditions and method: Cu/K-alpha 1 (target), 40 KV-40 mA (operating voltage and current), I(max)=2244, 2θ=5-60 degrees (scan range), 0.005/0.06 sec. (scanning speed), λ=1.54056.

The substantively pure crystal form E of regadenoson as provided in the present invention has an X-ray powder diffraction pattern as shown in FIG. 5.

In the present invention, infrared spectroscopy (IR) is further adopted to study and characterize the crystal form E of regadenoson. Instrument: BRUKER TENSOR27 Fourier-transform mid-infrared spectrometer (BRUKER Corp, Germany). Assay method: KBr pellet pressing method, with a spectrum range of 400 cm$^{-1}$-4000 cm$^{-1}$, and a resolution of 4 cm$^{-1}$.

The crystal form E of regadenoson provided in the present invention has an infrared spectrum as shown in FIG. 6, which is characterized in that, there are absorption peaks at 3331.71, 3215.54, 2927.97, 1648.75, 1604.99, 1577.42, 1530.74, 1492.24, 1447.33, 1409.03, 1380.47, 1343.48, 1286.87, 1234.77, 1205.30, 1188.55, 1125.28, 1092.61, 1060.80, 1025.93, 983.13, 910.61, 866.49, 810.21, 791.76, 725.68, 663.00, 632.69, 511.09 and 410.05 cm$^{-1}$ in the infrared spectrum.

It should be noted that, for the infrared spectrum peaks of the crystal form as described above, there might be some slight change from one instrument to another as well as from one sample to another, which might differ by about 1 unit, or by about 0.8 unit, or by about 0.5 unit, or by about 0.3 unit, or by about 0.1 unit. Therefore, the values as given cannot be deemed to be absolute.

The crystal form can also be characterized by other analytical technologies well known technically, such as differential scanning calorimetry (DSC). The substantively pure crystal form E of regadenoson provided in the present invention has a differential scanning calorimetric analysis curve as shown in FIG. 7, and has the properties that there is an absorption peak at about 221.02° C. in its differential scanning calorimetric analysis curve.

The present invention further provides a method for preparing crystal form E of regadenoson with a high purity free of residual solvents.

The preparation method of crystal form E of regadenoson provided in the present invention comprises dissolving regadenoson in N,N-dimethylformamide, adding a suitable amount of a polar solvent, and concentrating under a reduced pressure.

Preferably, the polar solvent is a low-boiling point polar solvent, that is a polar solvent with a boiling point below 100° C.

Further preferably, the polar solvent is dichloromethane, tetrahydrofuran, ethanol or acetonitrile.

The preparation method of crystal form E of regadenoson as described in the present invention provides a crystal form E with content>90%.

By thermogravimetric analysis of the crystal form E of regadenoson as described in the present invention, results show that the crystal form E of regadenoson as described in the present invention maintains the original crystal form unchanged; the content thereof and the total amount of impurities also have no significant change; and it begins to decompose at 237° C., has a good stability which is suitable for long-term storage.

The crystal form E of regadenoson as described in the present invention has excellent performances in terms of radionuclide myocardial perfusion imaging, and has a poor toxicity, good storage stability, and can be used for preparation of a medicament as a stress agent for radionuclide myocardial perfusion imaging. Therefore, the present invention provides use of the crystal form E of regadenoson in the preparation of a medicament for a stress agent for radionuclide myocardial perfusion imaging Further, the present invention provides a pharmaceutical preparation as a stress agent for radionuclide myocardial perfusion imaging, comprising the crystal form E of regadenoson.

BRIEF DESCRIPTION OF THE DRAWINGS

The configurations can be better understood with reference to the following drawings and description. The components in the figures are not necessarily to scale, emphasis instead being placed on illustrating the principles of the configurations. Moreover, in the figures, like reference numerals designate corresponding parts throughout the different views.

DETAILED DESCRIPTION OF THE INVENTION

Figure 1:
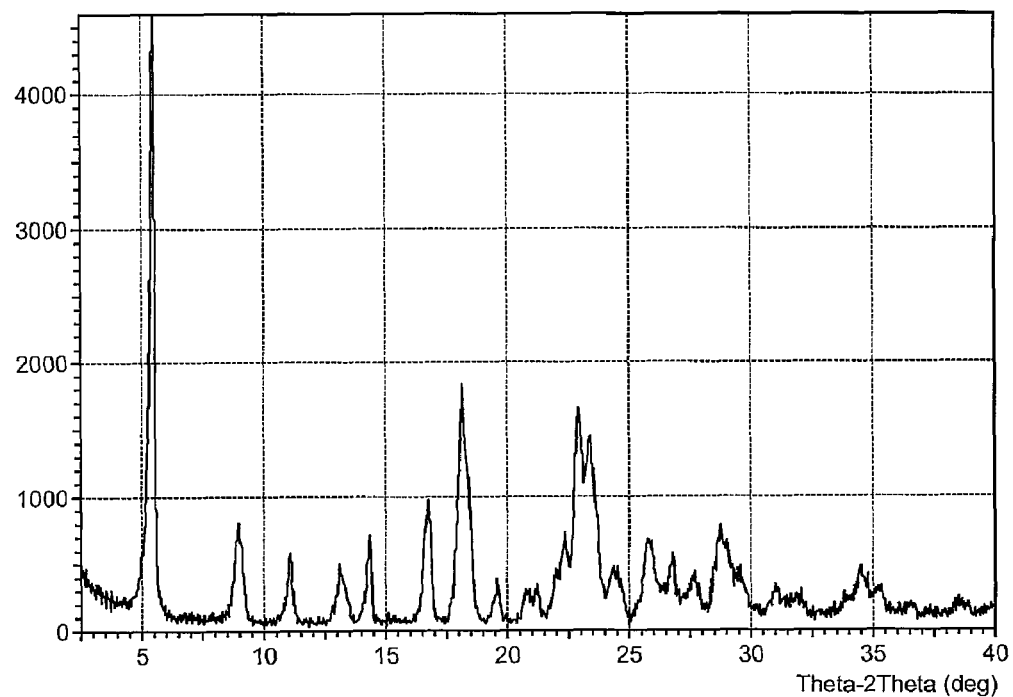
FIG. 1 shows an X-ray powder diffraction pattern of crystal form A of regadenoson as described in U.S. Pat. No. 7,732,595.
Figure 2:
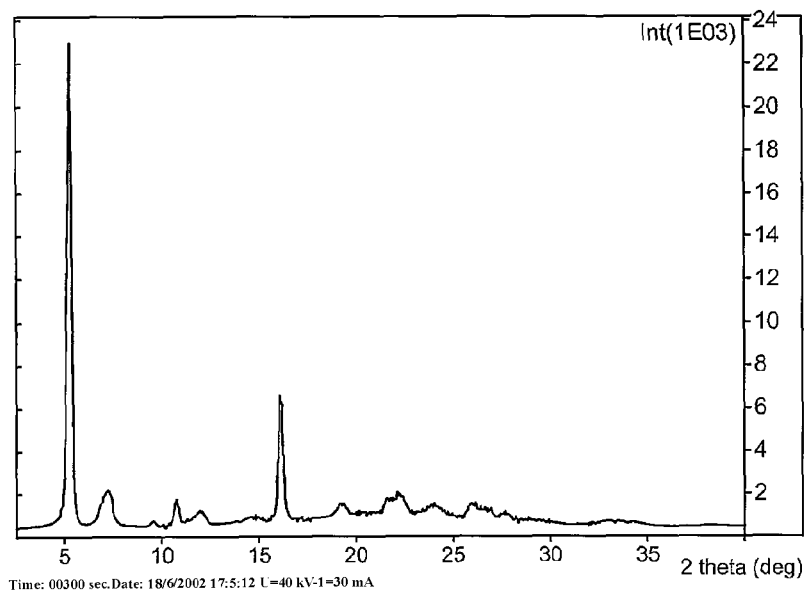
FIG. 2 shows an X-ray powder diffraction pattern of crystal form B of regadenoson as described in U.S. Pat. No. 7,732,595.
Figure 3:
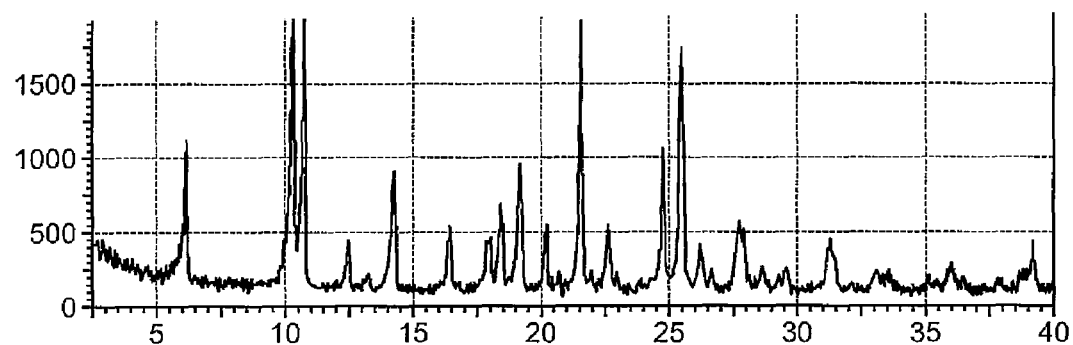
FIG. 3 shows an X-ray powder diffraction pattern of crystal form C of regadenoson as described in U.S. Pat. No. 7,732,595.
Figure 4:
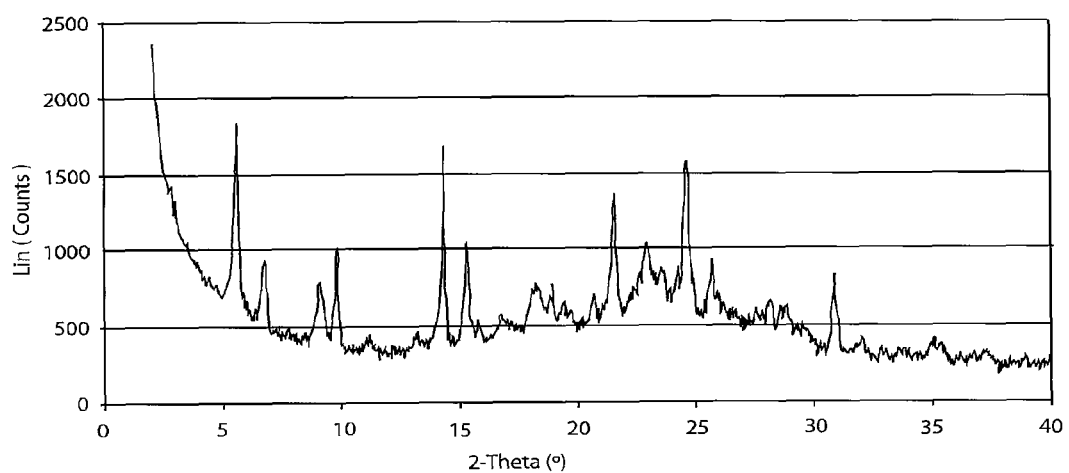
FIG. 4 shows an X-ray powder diffraction pattern of crystal form D of regadenoson as described in patent WO2012149196.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Examples of the present invention disclose a crystal form of regadenoson, as well as preparation methods and use thereof. In view of the disclosure herein, those skilled in the art can achieve it by properly improving process parameters. It is to be particularly noted that, all similar substitutions and modifications are obvious for those skilled in the art, all of which are deemed to be included within the present invention. The method of the present invention has been described by preferred examples, and thus those skilled in the art can obviously make modifications or suitable alterations and combinations to the method described herein without departing from the content, spirit and scope of the present invention, to achieve and apply the inventive technology.

For further understanding the present invention, the present invention will be illustrated in detail below in conjunction with the examples. The numerical ranges described in the description, such as the unit of measurement, reaction condition, physical status of a compound or percentage, are all used to provide clear and correct written references. Those skilled in the art, when putting the present invention into practice, can still obtain expected results by using a temperature, concentration, amount or the like outside such ranges or being different from an individual value.

EXAMPLE 1

Figure 5:
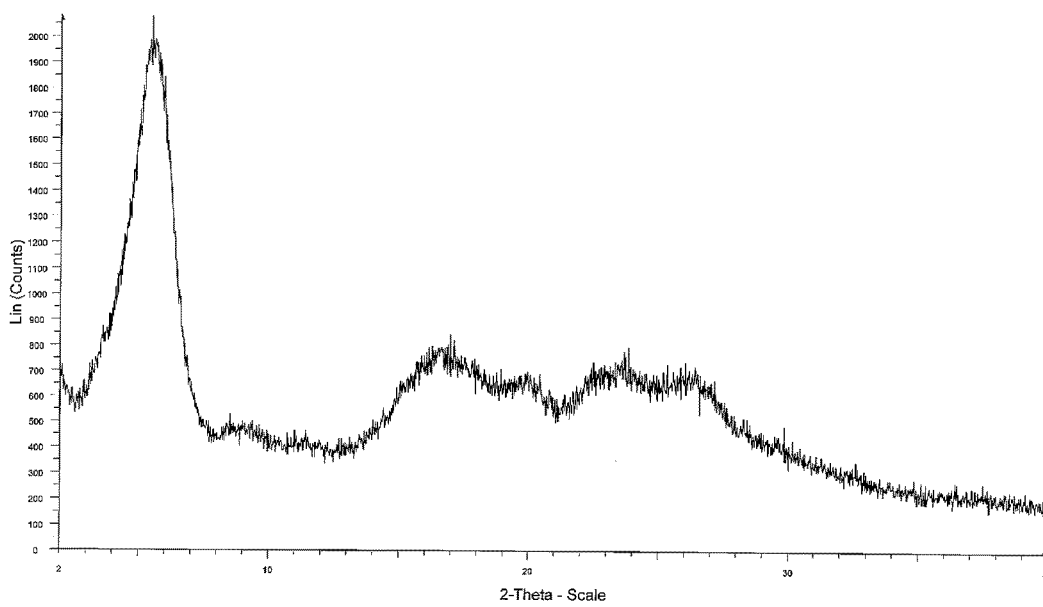
FIG. 5 shows an X-ray powder diffraction pattern of crystal form E of regadenoson provided in example 1 of the present invention, which is obtained by irradiation with Cu/Kα rays, in which X-ray powder diffraction pattern, the vertical ordinate represents diffraction intensity expressed in count per second (cps), and the horizontal ordinate represents diffraction angle 2θ expressed in degree.
Figure 6:
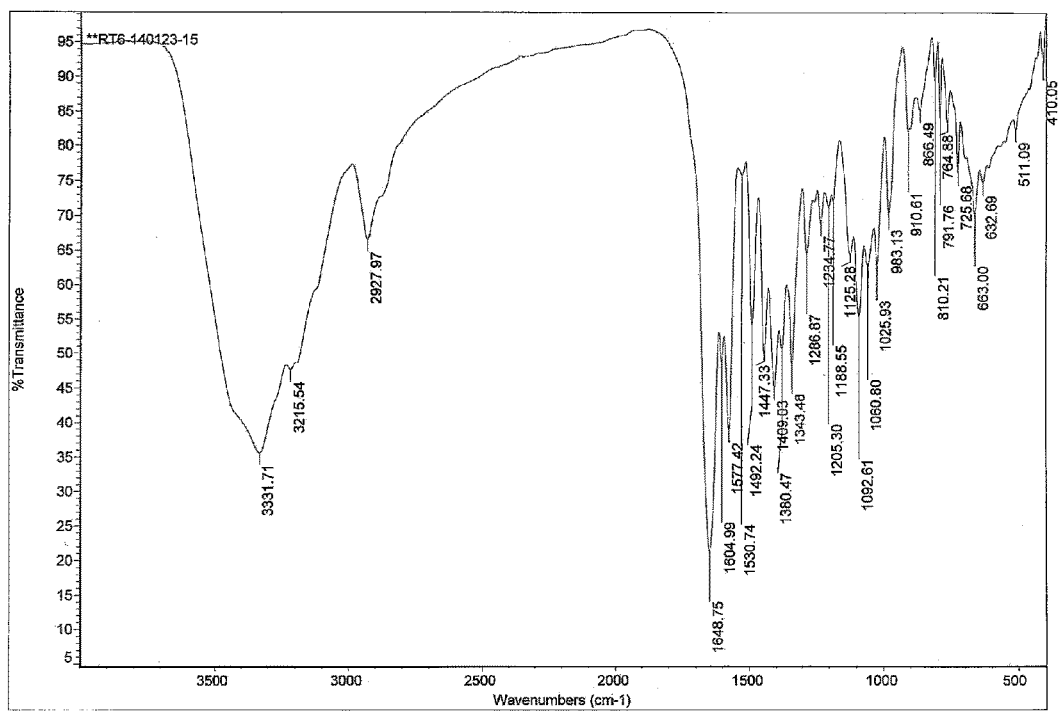
FIG. 6 is an infrared spectrum of the crystal form E of regadenoson provided in example 1 of the present invention, in which the vertical ordinate represents transmittance (T) in percentage (%), and the horizontal ordinate represents wave number in cm$^{-1}$.

Preparation of Crystal Form E of Regadenoson 1 g of regadenoson was dissolved into 10 ml DMF, to which 10 ml dichloromethane was added, concentrated under reduced pressure at 50° C., to obtain 1 g of crystal form E of regadenoson with a content of 92%. The X-ray powder diffraction pattern and infrared spectrum of this crystal form are shown in FIGS. 5 and 6, respectively.

EXAMPLE 2

Preparation of Crystal Form E of Regadenoson 1 g of regadenoson was dissolved into 10 ml DMF, to which 10 ml tetrahydrofuran was added, concentrated under reduced pressure at 50° C., to obtain 1 g of crystal form E of regadenoson with a content of 91%. The X-ray powder diffraction pattern and infrared spectrum of this crystal form are consistent with those in EXAMPLE 1.

EXAMPLE 3

Preparation of Crystal Form E of Regadenoson 1 g of regadenoson was dissolved into 10 ml DMF, to which 5 ml ethanol was added, concentrated under reduced pressure at 50° C., to obtain 1 g of crystal form E of regadenoson with a content of 91%. The X-ray powder diffraction pattern and infrared spectrum of this crystal form are consistent with those in EXAMPLE 1.

EXAMPLE 4

Preparation of Crystal Form E of Regadenoson 1 g of regadenoson was dissolved into 10 ml DMF, to which 5 ml acetonitrile was added, concentrated under reduced pressure at 50° C., to obtain 1 g of crystal form E of regadenoson with a content of 93%. The X-ray powder diffraction pattern and infrared spectrum of this crystal form are consistent with those in EXAMPLE 1.

EXAMPLE 5

Differential Scanning Calorimetry Analysis of Crystal Form E of Regadenoson

The crystal form E of regadenoson prepared in example 1 was studied and characterized by using differential scanning calorimetry (DSC). The test conditions for the differential scanning calorimetry analysis were as the following: instrument: DSC 204F1 (Germany) differential scanning calorimeter; sample weight: 8.17 mg; heating rate: 2° C./min; the highest temperature: 250° C.; nitrogen flow rate: 20 mL/min Results are shown in FIG. 7.

Figure 7:
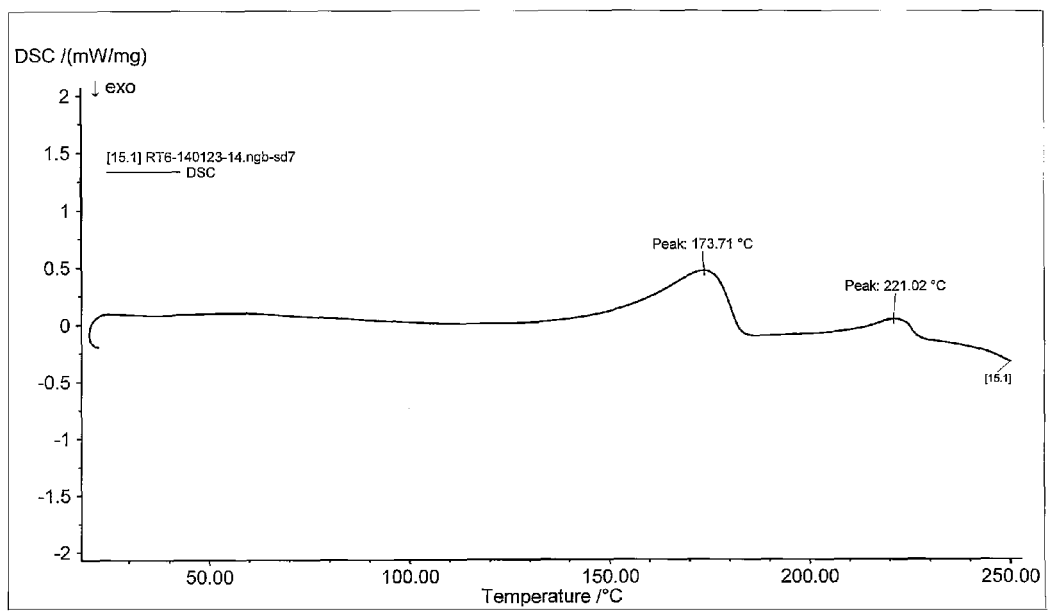
FIG. 7 is a curve of differential scanning calorimetry (DSC) of the crystal form E of regadenoson provided in example 1 of the present invention, in which the vertical ordinate represents the rate of heat flow in calorie/second, and the horizontal ordinate represents temperature in ° C.

From the results in FIG. 7, it can be seen that, when the temperature reaches up to 173.71° C., there is a significant temperature absorption reaction; when it reaches up to 221° C., there is a slight temperature absorption, after which the sample begins to decompose. The solvents for the crystal form E of regadenoson as described in the present invention are all solvents with low boiling points, thus the reaction at 173.71° C. is the temperature reaction caused by dehydration of crystal water.

EXAMPLE 6

Thermogravimetric Analysis of Crystal Form E of Regadenoson

The crystal form E of regadenoson prepared in example 1 was studied and characterized by using thermogravimetric analysis (TGA). Test conditions for the thermogravimetric analysis were as the following: instrument: Pyris 1 TGA thermogravimetric analyzer (U.S.); sample amount: 4.457 mg; heating rate under nitrogen protection: 10° C./min; temperature range: 30° C.-600° C.; nitrogen flow rate: 20 mL/min. Results are shown in FIG. 8.

Figure 8:
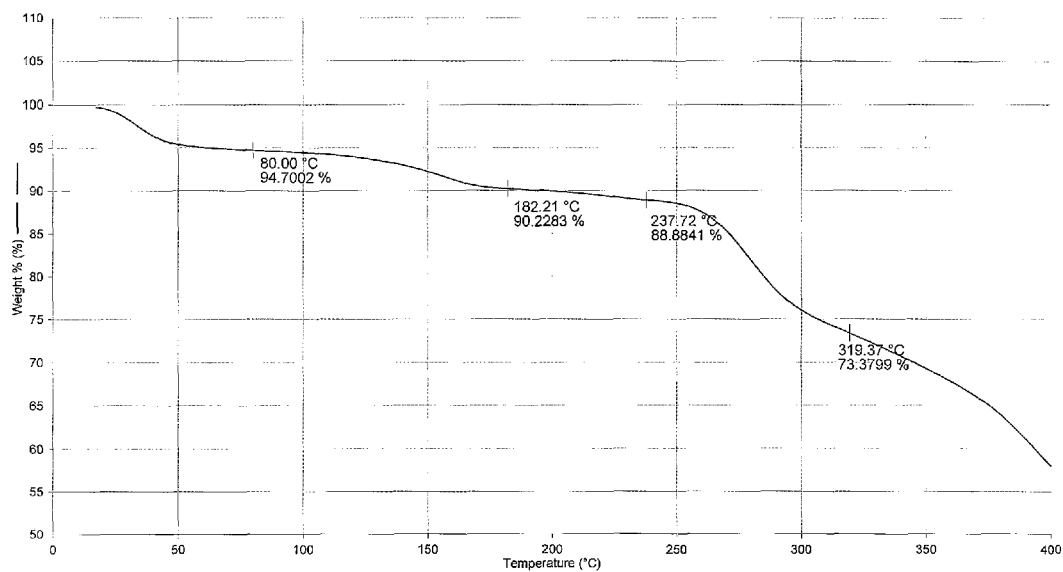
FIG. 8 shows a thermogravimetric analysis diagram of the crystal form E of regadenoson provided in example 1 of the present invention, wherein the straight line is a curve of thermogravimetric analysis in which the vertical ordinate represents percentage of weight retention and the horizontal ordinate represents temperature in ° C.; and the dotted line is a differential curve of thermogravimetric analysis in which the vertical ordinate represents rate of weight change in %/min and the horizontal ordinate represents temperature in ° C.

From the results in FIG. 8, it can be seen that, weight loss is 5.3% at 80° C., with a weight loss rate of 2.1%/min; weight loss is 4.5% at 182.21° C., with a weight loss rate of 0.39%/min; when the temperature reaches up to 237° C., continuous weight loss appears, after which the weight loss percentage is rapidly increased. From the analysis results, it is believed that weight loss at 80° C. should correspond to the low-boiling point polar solvent residue; and weight loss at 182.21° C. should correspond to crystal water in the sample; while weight loss at 237° C. means that the sample begins to decompose. The results show that the crystal form E of regadenoson as described in the present invention decomposes when heated up to 237° C., and has a good stability, which is suitable for long-term storage.

The above examples are illustrated only to facilitate understanding the method of the present invention and the core principle thereof. It should be noted that, for those of ordinary skill in the art, several improvements and modifications can also be made without departing from the principle of the present invention, which also fall within the protection scope of the claims thereof.

What is claimed is:

1. A crystal form E of regadenoson, which is characterized in that, it has an X-ray powder diffraction pattern substantively as shown in FIG. 5; and an absorption peak at about 221.02° C. in differential scanning calorimetric analysis curve thereof.

2. The crystal form E according to claim 1, which is characterized in that, there are absorption peaks at 3331.71, 3215.54, 2927.97, 1648.75, 1604.99, 1577.42, 1530.74, 1492.24, 1447.33, 1409.03, 1380.47, 1343.48, 1286.87, 1234.77, 1205.30, 1188.55, 1125.28, 1092.61, 1060.80, 1025.93, 983.13, 910.61, 866.49, 810.21, 791.76, 725.68, 663.00, 632.69, 511.09 and 410.05 cm$^{-1}$ in infrared spectrum thereof.

3. A method for preparing the crystal form E of regadenoson according to claim 1, characterized by dissolving regadenoson in N,N-dimethylformamide, adding a suitable amount of a polar solvent, and then concentrating under reduced pressure, to obtain the crystal form E of regadenoson.

4. The preparation method according to claim 3, which is characterized in that, the polar solvent is dichloromethane, tetrahydrofuran, ethanol or acetonitrile.

5. A method for radionuclide myocardial perfusion imaging comprising use of the crystal form E of regadenoson according to claim 1 by adding the crystal form E of regadenoson according to claim 1 to a pharmaceutical preparation.

6. A pharmaceutical preparation for radionuclide myocardial perfusion imaging, characterized by comprising the crystal form E of regadenoson according to claim 1.

* * * * *

UNITED STATES PATENT AND TRADEMARK OFFICE
CERTIFICATE OF CORRECTION

| | | |
|---|---|---|
| PATENT NO. | : 9,809,617 B2 | Page 1 of 1 |
| APPLICATION NO. | : 14/791290 | |
| DATED | : November 7, 2017 | |
| INVENTOR(S) | : Wei Liu et al. | |

It is certified that error appears in the above-identified patent and that said Letters Patent is hereby corrected as shown below:

On the Title Page

Item (54) and in the Specification, Column 1, Lines 1-2 The title is currently "CRYSTAL FORM OF REGADENOSON AND PREPARATION METHOD THEREOF".

The correct title is "A CRYSTAL FORM OF REGADENOSON AND PREPARATION METHOD THEREOF".

Signed and Sealed this
Twenty-seventh Day of August, 2024

Katherine Kelly Vidal
*Director of the United States Patent and Trademark Office*